United States Patent [19]

Tamano et al.

[11] Patent Number: 5,585,213
[45] Date of Patent: Dec. 17, 1996

[54] HOLE-TRANSPORTING MATERIAL AND ITS USE

[75] Inventors: Michiko Tamano; Toshikazu Onikubo; Toshio Enokida, all of Tokyo, Japan

[73] Assignee: Toyo Ink Manufacturing Co., Ltd., Tokyo, Japan

[21] Appl. No.: 466,971

[22] Filed: Jun. 6, 1995

[30] Foreign Application Priority Data

| Jun. 10, 1994 | [JP] | Japan | 6-128752 |
| Jun. 10, 1994 | [JP] | Japan | 6-128753 |
| Jun. 10, 1994 | [JP] | Japan | 6-128754 |

[51] Int. Cl.$^6$ .................................. G03G 5/047
[52] U.S. Cl. ............................ 430/59; 540/143
[58] Field of Search ................ 430/58, 59; 540/141, 540/143

[56] References Cited

U.S. PATENT DOCUMENTS

| 3,895,944 | 7/1975 | Wiedemann et al. | 430/59 |
| 4,471,039 | 9/1984 | Borsenberger | 430/59 |
| 5,334,714 | 8/1994 | Oguchi et al. | 540/143 |

FOREIGN PATENT DOCUMENTS

| 0044686 | 1/1982 | European Pat. Off. . |
| 0284370 | 9/1988 | European Pat. Off. . |
| 0305938 | 3/1989 | European Pat. Off. . |
| 0373643 | 6/1990 | European Pat. Off. . |

*Primary Examiner*—John Goodrow
*Attorney, Agent, or Firm*—Wenderoth, Lind & Ponack

[57] ABSTRACT

A hole-transporting material having excellent hole transportation capability and excellent durability, and an organic EL device and an electrophotographic photoconductive drum for which the above hole-transporting material is adapted and which have excellent stability in the repetitive use.

12 Claims, 1 Drawing Sheet

HOLE-TRANSPORTING MATERIAL AND ITS USE

FIELD OF THE INVENTION

The present invention relates to a hole-transporting material having a phthalocyanine structure. More specifically, it relates to a hole-transporting material used as a photosensitive material or an organic electrically conductive material, specifically, a hole-transporting material for an organic electroluminescence (EL) device used in a flat light source or display or an electrophotographic photoreceptor.

PRIOR ART OF THE INVENTION

Organic photoconductive materials developed as photosensitive materials or hole-transporting materials are advantageous in that they can be produced at a low cost, can be easily processed in diversified ways and are free of pollution. There have been proposed many organic photoconductive materials such as an oxadiazole derivative (U.S. Pat. No. 3,189,447), an oxazole derivative (U.S. Pat. No. 3,257,203), hydrazone derivatives (U.S. Pat. No. 3,717,462, JP-A-54-59143 and U.S. Pat. No. 4,150,978), triarylpyrazoline derivatives (U.S. Pat. No. 3,820,989, JP-A-51-93224 and JP-A-55-108667), arylamine derivatives (U.S. Pat. No. 3,180,730, U.S. Pat. No. 4,232,103, JP-A-55-144250 JP-A-56-119132) and stilbene derivatives (JP-A-58-190953 and JP-A-59-195658).

An organic EL device is one of the products produced by technology using a hole-transporting material. An EL device formed of an organic substance is expected to be used as an inexpensive large-area full-color display device of a solid light-emission type, and has been and is developed in various ways. Generally, an EL device has a structure in which a light-emitting layer is sandwiched with opposing electrodes. Light emission is the following phenomenon. When an electric field is applied between these two electrodes, electrons are implanted from the cathode side, and holes are implanted from the anode side. Further, electrons arc recombined with holes in the light-emitting layer, and energy is emitted as light when their energy levels are shifted back from a conduction band to a valence band.

Conventional organic EL devices require a higher actuation voltage than inorganic EL devices, and their brightness of emitted light and light emission efficiency are also lower than those of inorganic EL devices. Further, conventional organic EL devices greatly deteriorate in properties, and almost no organic EL devices have been put to practical use.

A recent report says that an organic EL device emits light at a low voltage of less than 10 V and has a thin film containing an organic compound having high fluorescent quantum efficiency, and this organic EL device attracts attention (Applied Physics Letters, Vol. 51, page 913, 1987).

In the above organic EL device, green light having a high brightness is obtained by using a metal chelate complex as a fluorescence layer and an amine-containing compound as a hole-implanting layer. The above organic EL device has performance almost equivalent to that required for practical use. That is, the brightness is hundreds cd/m² at a direct current voltage of 6–7 V, and the maximum light emission efficiency is 1.51 m/W.

However, organic EL devices which have been so far developed have no sufficient light emission brightness although they are improved in light emission intensity by improving their constitutions. Further, those organic EL devices have a large problem in that they are poor in stability in the repetitive use. It is therefore desired to develop a hole-transporting material having excellent charge transportation capability and excellent durability for developing an organic EL device showing a higher light emission brightness and excellent stability in the repetitive use.

Further, an electrophotographic photorecptor is one of the products for which a hole-transporting material is adapted. An electrophotographic method is one image-forming method that was invented by Carlson. In the electrophotographic method, an electrophotographic photorecpor is charged by corona discharging, then an electrostatic latent image is formed on the electrophotographic photoreceptor by optical exposure to an image, a toner is allowed to adhere to the electrostatic latent image to develop an image, and the so-obtained image of the toner is transferred to a receptor. The basic requirements of the electrophotographic photoreceptor used in the above electrophotographic method are that a proper potential is maintained in a dark place, that the degree of discharging of electric charge in a dark place is low, and that the electric charge is readily discharged by optical exposure. A conventional electrophotographic photoreceptor is formed of an inorganic photoconductive material such as selenium, selenium alloy, zinc oxide, cadmium sulfide or tellurium. These inorganic materials are advantageous in that they have high durability and permit the reproduction of a large number of copies, while it is pointed out that they have defects in that the production cost increases, that their processability is poor and that they are toxic. For overcoming these defects, organic electrophotographic photoreceptors have been developed, while, at present, it cannot be necessarily said that electrophotographic photoreceptors for which conventional organic photoconductive materials as hole-transporting materials are adapted are satisfactory in electrophotographic characteristics such as chargeability, sensitivity and residual potential. It is therefore desired to develop a hole-transporting material having excellent charge transportation capability and excellent durability.

SUMMARY OF THE INVENTION

It is an object of the present invention to provide a hole-transporting material having excellent hole transportation capability and excellent durability.

It is another object of the present invention to provide an organic EL device and an electrophotographic photoconductive drum for which the hole-transporting material of the present invention is adapted and which have excellent stability in the repetitive use.

According to the present invention, there is provided a hole-transporting material of the formula (1),

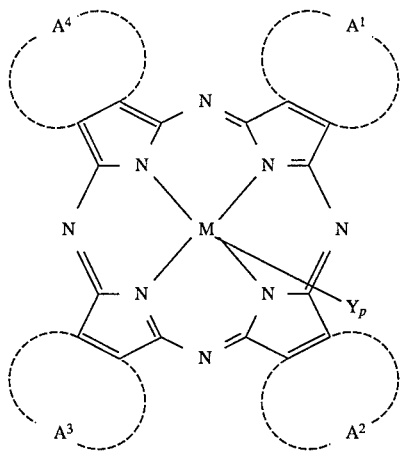

wherein:
each of rings $A^1$ to $A^4$ is a substituted alicyclic group, an unsubstituted alicyclic group, a substituted aromatic group, an unsubstituted aromatic group, a substituted heterocyclic aromatic group, an unsubstituted heterocyclic aromatic group, a substituted heterocyclic ring or an unsubstituted heterocyclic ring, Y is, or each of the Ys are independently, a substituent of any one of the formulae (2) to (13),

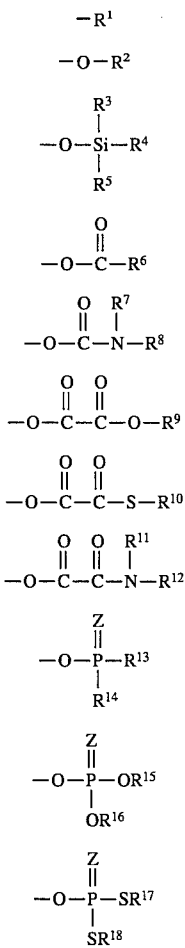

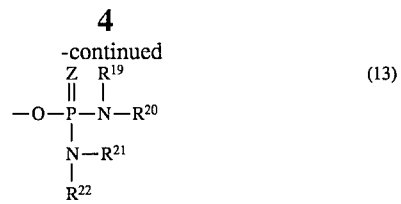

in which each of $R^1$ to $R^{22}$ is independently hydrogen (provided that $R^1$, $R^{13}$ and $R^{14}$ are excluded), substituted aliphatic group, an unsubstituted aliphatic group, a substituted alicyclic group, an unsubstituted alicyclic group, a substituted aromatic group, an unsubstituted aromatic group, a substituted heterocyclic aromatic group, an unsubstituted heterocyclic aromatic group, a substituted heterocyclic group or an unsubstituted heterocyclic group, and Z is oxygen or sulfur, P is an integer of 1 or 2, and M is a metal atom having a valence of 3 or 4.

Further, according to the present invention, there is provided an organic electroluminescence device comprising a pair of electrodes and a light-emitting layer of at least one thin film formed of an organic compound, sandwiched between a pair of the electrodes, wherein at least one thin film forming the light-emitting layer contains the above hole-transporting material.

Further, according to the present invention, there is provided an electrophotographic photoreceptor comprising an electrically conductive substrate and a photosensitive layer formed on the substrate, the photosensitive layer containing the above hole-transporting material.

DETAILED DESCRIPTION OF THE INVENTION

Figure 1:
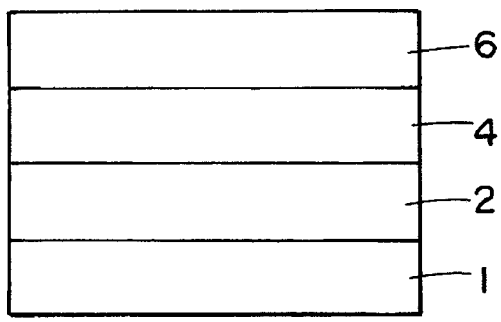
FIG. 1 is a schematic cross section of an organic EL device having a light-emitting layer sandwiched between a pair of electrodes.

The hole-transporting material of the present invention has the above formula (1). In the formula (1), each of the rings $A^1$ to $A^4$ is independently a substituted alicyclic group, an unsubstituted alicyclic group, a substituted aromatic group, an unsubstituted aromatic group, a substituted heterocyclic aromatic group, an unsubstituted heterocyclic aromatic group, a substituted heterocyclic ring or an unsubstituted heterocyclic ring.

Specific examples of the alicyclic group include cyclopentane and cyclohexene. Specific examples of the aromatic group include benzene, naphthalene and anthracene. Specific examples of the heterocyclic aromatic group include pyridine, pyrazine, pyrimidine, triazine and quinoxaline.

Specific examples of the heterocyclic ring include pyrrolidine, dioxane, piperidine and morpholine.

Specific examples of the substituent on the above rings include halogen atoms such as chlorine, bromine, iodine and fluorine; substituted or unsubstituted alkyl groups such as methyl, ethyl, propyl, butyl, sec-butyl, tert-butyl, pentyl, hexyl, heptyl, octyl, stearyl and trichloromethyl; substituted or unsubstituted aryl groups such as phenyl, naphthyl, 3-methylphenyl, 3-methoxyphenyl, 3-fluorophenyl, 3-trichloromethylphneyl, 3-trifluoromethylphenyl and 3-nitrophenyl; substituted or unsubstituted alkoxy groups such as methoxy, n-butoxy, tert-butoxy, trichloromethoxy, trifluoroethoxy, pentafluoropropoxy, 2,2,3,3-tetrafluoropropoxy, 1,1,1,3,3,3-hexafluoro-2-propoxy and 6-(perfluoroethyl) hexyloxy; substituted or unsubstituted aryloxy groups such as phenoxy, p-nitrophenoxy, p-tertbutylphenoxy, 3-fluorophenoxy, pentafluorophenoxy and 3-trifluoromethylphenoxy; substituted or unsubstituted alkylthio groups such as methylthio, tert-butylthio, hexylthio, octylthio and trifluoromethylthio; substituted or unsubstituted arylthio groups such as phenylthio, p-nitrophenylthio, p-tert-butylphenylthio, 3-fluorophenylthio, pentafluorophenylthio and 3-trifluoromethylphenylthio; mono- or disubstituted amine groups such as cyano, nitro, amine, methylamine, dimethylamino, ethylamine, diethylamino, dipropylamino, dibutylamino and diphenylamino; acylamino groups such as bis(acetoxymethyl)amino, bis(acetoxyethyl)amino, bis(acetoxypropyl)amino and bis(acetoxybutyl)amine; carbamoyl groups such as hydroxyl, siloxy, acyl, methylcarbamoyl, dimethylcarbamoyl, ethylcarbamoyl, diethylcarbamoyl, propylcarbamoyl, butylcarbamoyl and phenylcarbamoyl; alicyclic groups such as carboxyl, sulfonic group, imido, cyclopentyl and cyclohexyl, aromatic groups such as phenyl, naphthyl and biphenyl; heterocyclic aromatic groups such as pyridyl, pyrazinyl, pyrimidyl, pyridazinyl, triazinyl, indolyl, quinolyl and acridinyl; and heterocyclic ring groups such as pyrrolidinyl, dioxanyl, piperidinyl, morpholyl, piperazinyl and trithianyl.

The central metal M can be selected from metal atoms having a valence of 3 or 4, while Al, Ga, In, Si, Ge or Sn is preferred.

Typical examples of $R^1$ to $R^{22}$ in the formulae (2) to (13) include substituted or unsubstituted aliphatic groups such as methyl, ethyl, n-butyl, tert-butyl, stearyl, trichloromethyl, trifluoromethyl, 2,2,2-trifluoroethyl, 2,2,3,3-tetrafluoropropyl, 2,2,3,3,3-pentafluoropropyl, 1,1,1,3,3,3-hexafluoro-2-propyl, 2,2,3,3,4,4-hexafluorobutyl and 2-methoxyethyl; substituted or unsubstituted alicyclic groups such as cyclopentyl and cyclohexyl; substituted or unsubstituted aromatic groups such as phenyl, naphthyl, biphenyl, p-nitrophenyl, p-tert-butylphenyl and pentafluorophenyl; heterocyclic aromatic groups such as pyridine, pyrazine, pyrimidine, pyridazine, triazine, indole, quinoline and acridine; and substituted or unsubstituted heterocyclic rings such as pyrrolidine, dioxane, piperidine, morpholine, piperazine and trithiane. Examples of the substituent on the $R^1$ to $R^{22}$ substituents include those described as substituents on the above rings. Further, in the formula (6), $R^7$ and $R^8$ may be members forming a five-membered or six-membered ring containing a nitrogen atom. In the formula (9), $R^{11}$ and $R^{12}$ may be members forming a five-membered or six-membered ring containing a nitrogen atom.

The compound of the formula (1), provided by present invention, can be produced, for example, by the following method.

First, a phthalocyanine compound of the formula (16) can be produced from a phthalonitrile of the formula (14), an isoindoline compound of the formula (15), a corresponding phthalic acid anhydride or a phthalimide and a salt of a metal selected from the metals specified as M in the formula (1) as starting materials by a conventional method.

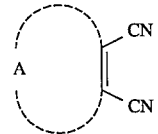

(14)

wherein a ring A has the same meaning as those of the rings $A^1$ to $A^4$ in the formula (1).

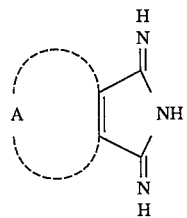

(15)

wherein a ring A has the same meaning as those of the rings $A^1$ to $A^4$ in the formula (1).

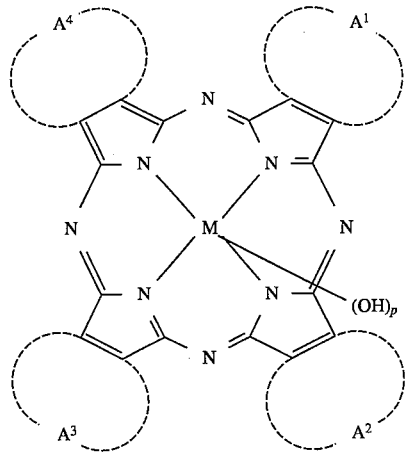

(16)

wherein $A^1$ to $A^4$ are as defined in the formula (1).

Then, the phthalocyanine compound of the formula (16) is reacted with an alcohol, a trialkylsilanol, an acylating agent, an oxalyl chloride derivative or a chlorophosphine derivative having a linear, branched or cyclic alkyl group which may have a substituent or an aryl group, to give the phthalocyanine compound of the above formula (1).

Typical examples of the compound (hole-transporting material) of the formula (1) are as follows, although the compound of the formula (1) shall not be specially limited thereto.

| Compound | Chemical Structure |
|---|---|
| (1) | [phthalocyanine-like macrocycle with central Si, axial CH₃O and OCH₃ groups] |
| (2) | [phthalocyanine-like macrocycle with central Si, axial phenyl groups] |
| (3) | [phthalocyanine-like macrocycle with central Al, axial HO group] |

-continued
| Compound | Chemical Structure |
|---|---|
| (4) | 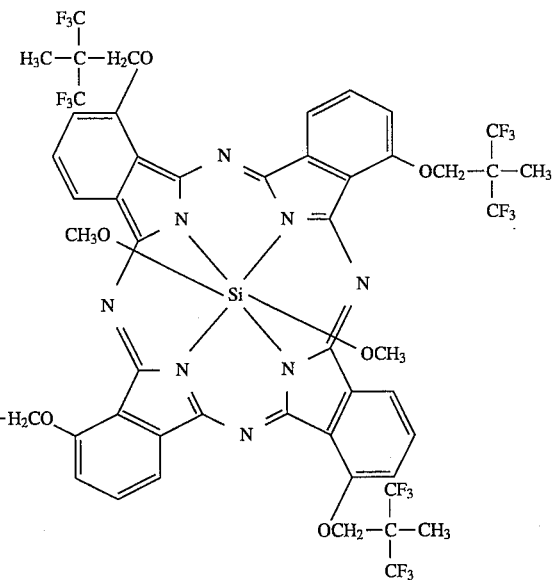 |
| (5) | 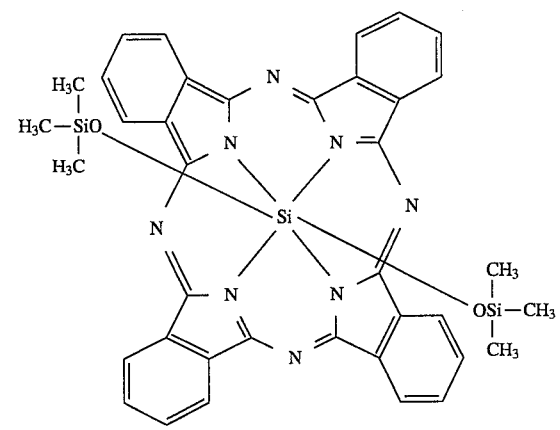 |
| (6) | 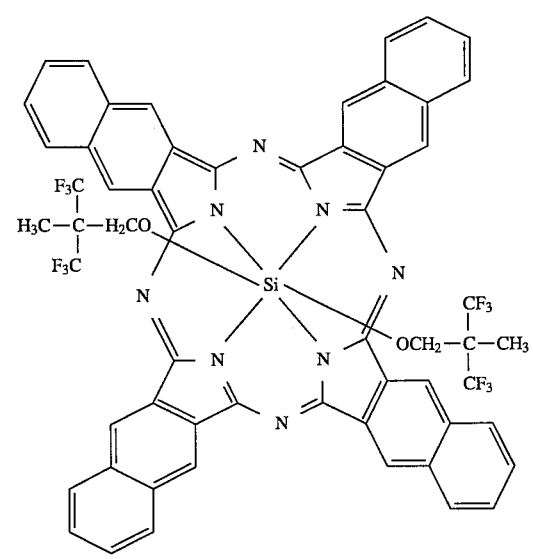 |

| Compound | Chemical Structure |
|---|---|
| (7) | *structure: silicon phthalocyanine-type complex with Me, COOH, COOCH₃, CH₃COO, HO, HOCO, cyclohexyl substituents* |
| (8) | *structure: silicon phthalocyanine-type complex with Br, NO₂, CH₃O, OCH₃ substituents* |
| (9) | *structure: tin phthalocyanine-type complex with Br, F-phenoxy, CH₃O substituents* |

| Compound | Chemical Structure |
|---|---|
| (10) | 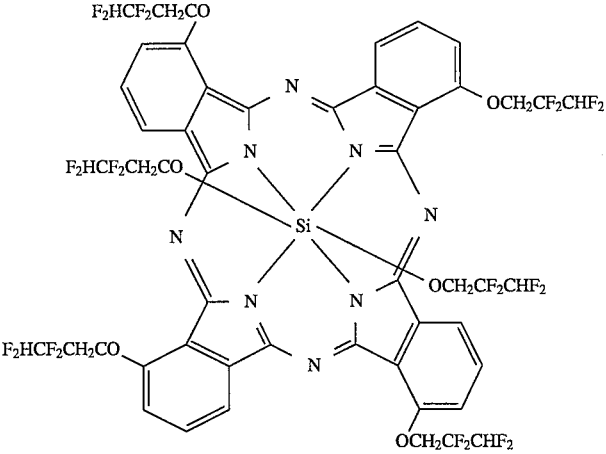 |
| (11) | 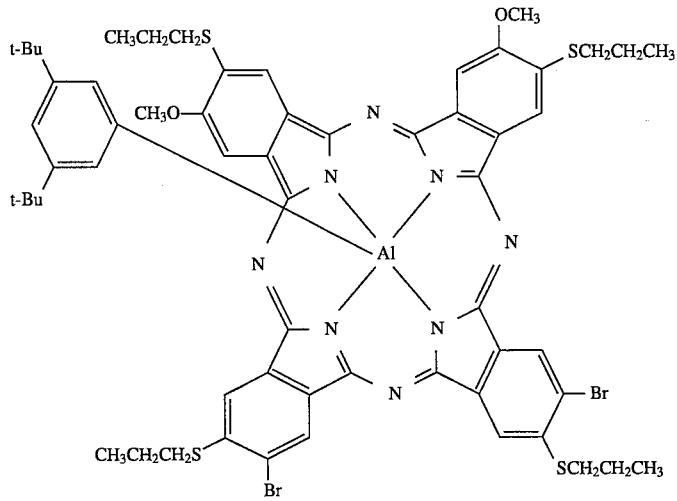 |
| (12) | 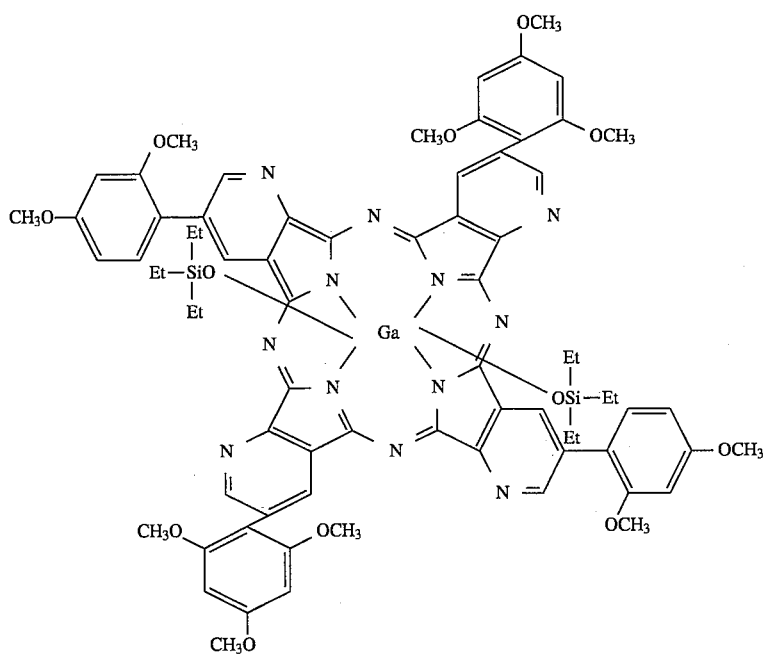 |

-continued
| Compound | Chemical Structure |
|---|---|
| (13) | 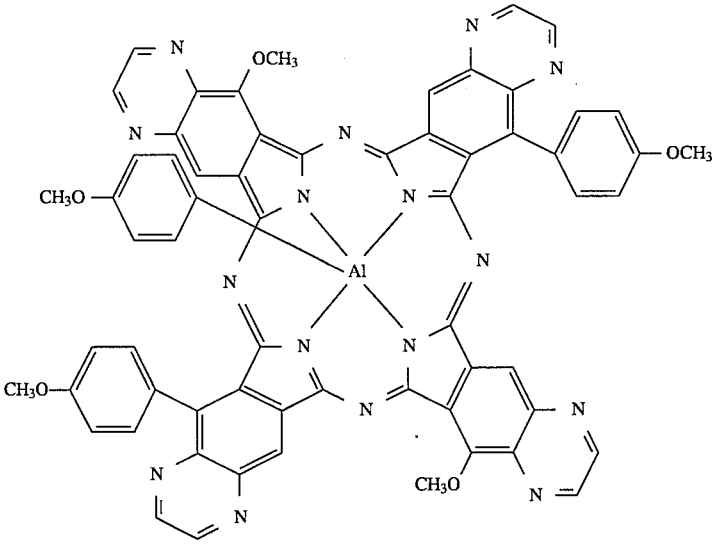 |
| (14) | 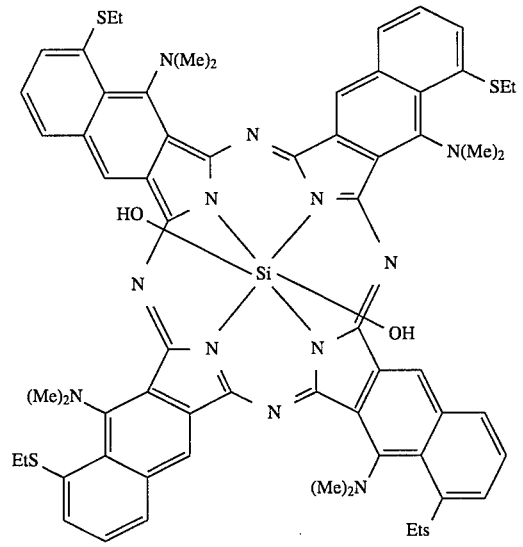 |

-continued
| Compound | Chemical Structure |
|---|---|
| (15) | 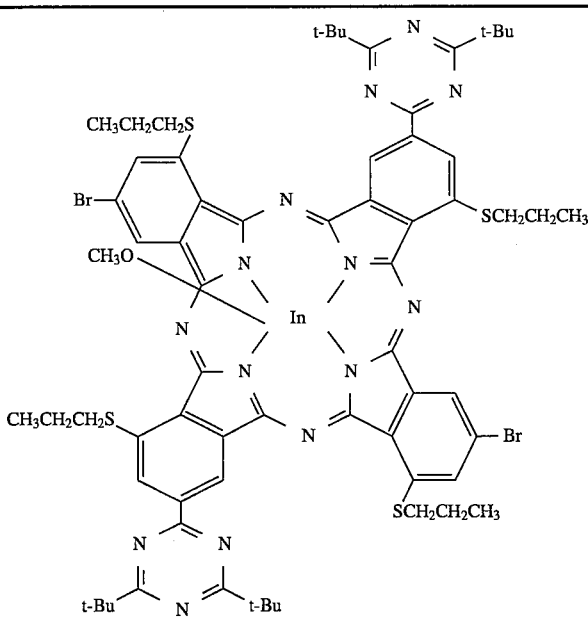 |
| (16) | 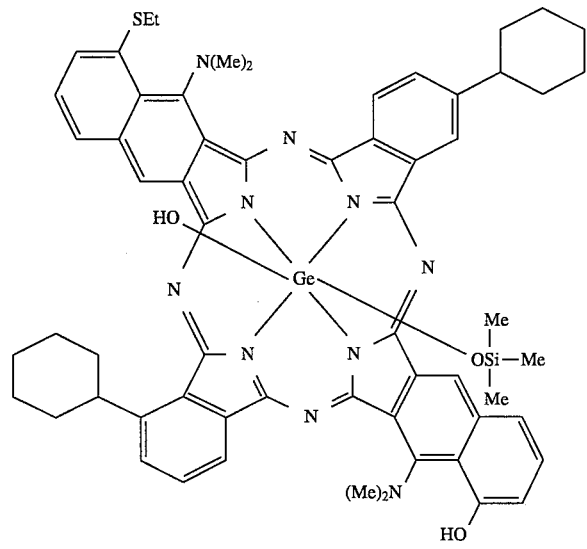 |
| (17) | 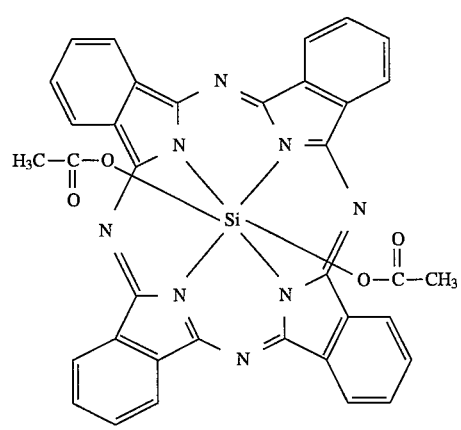 |

| Compound | Chemical Structure |
|---|---|
| (18) | *[phthalocyanine Al complex with dimethylcarbamoyl-carbonyloxy axial ligand]* |
| (19) | *[phthalocyanine Si complex with two dimethylcarbamoyl-carbonyloxy axial ligands]* |
| (20) | *[naphthalocyanine Al complex with phenylthio-oxalyloxy axial ligand]* |

-continued

| Compound | Chemical Structure |
|---|---|
| (21) | 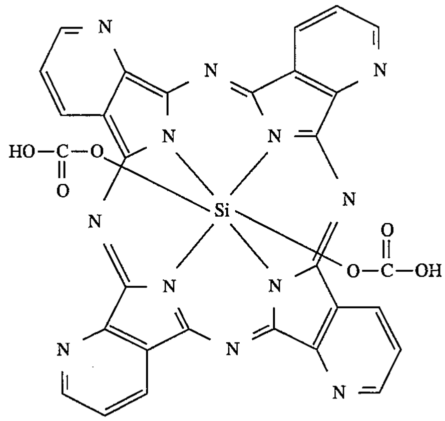 |
| (22) | 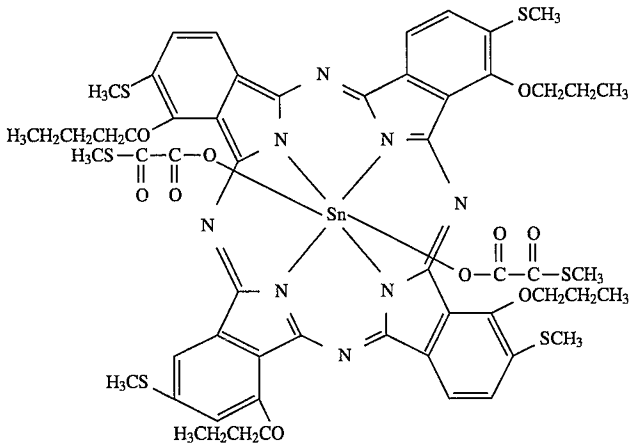 |
| (23) | 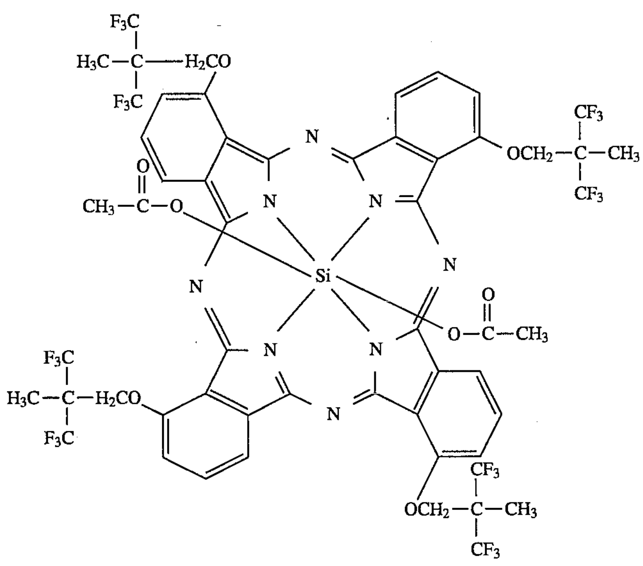 |

-continued
| Compound | Chemical Structure |
|---|---|
| (24) | 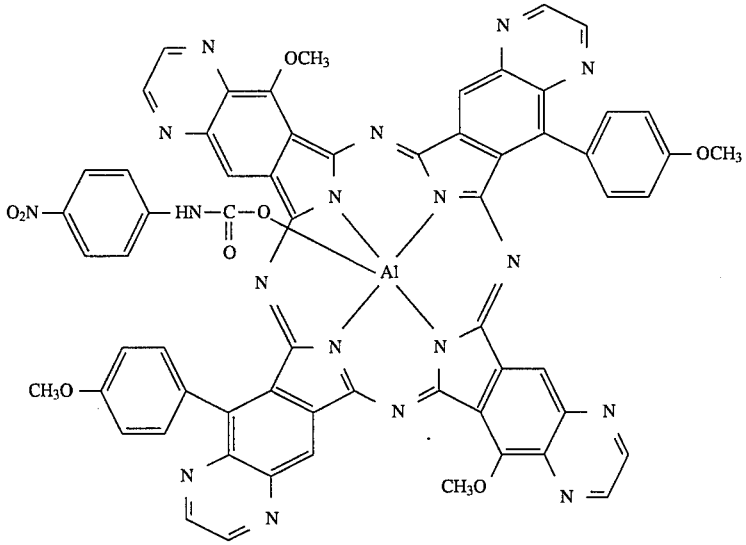 |
| (25) | 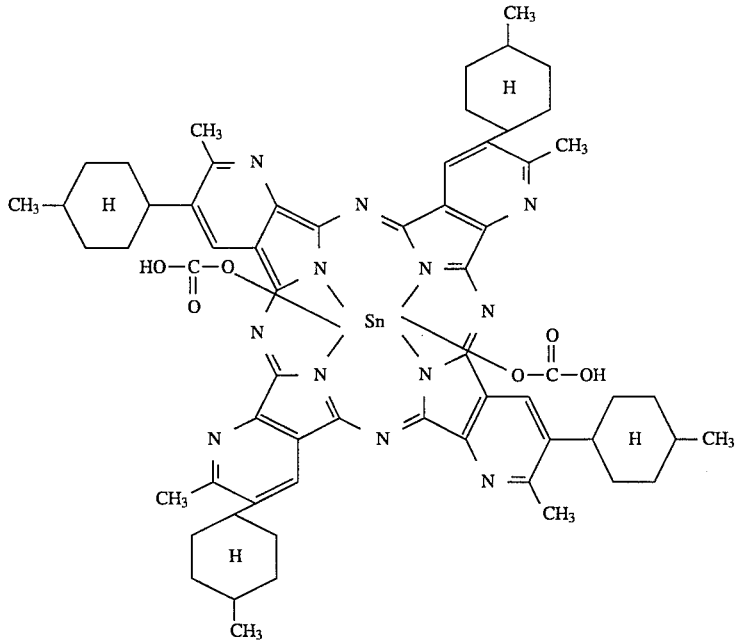 |
| (26) | 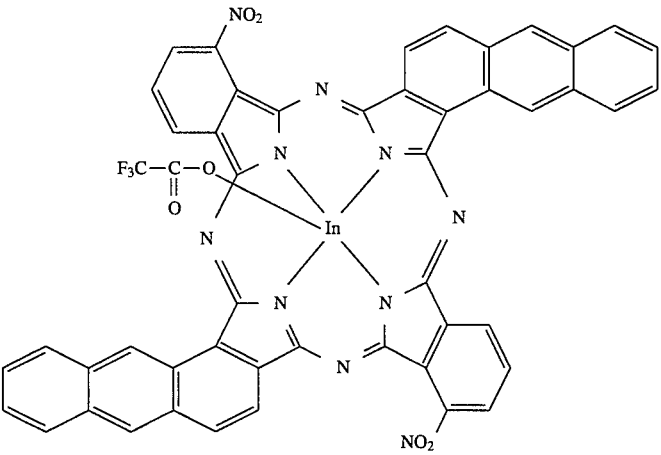 |

| Compound | Chemical Structure |
|---|---|
| (27) | 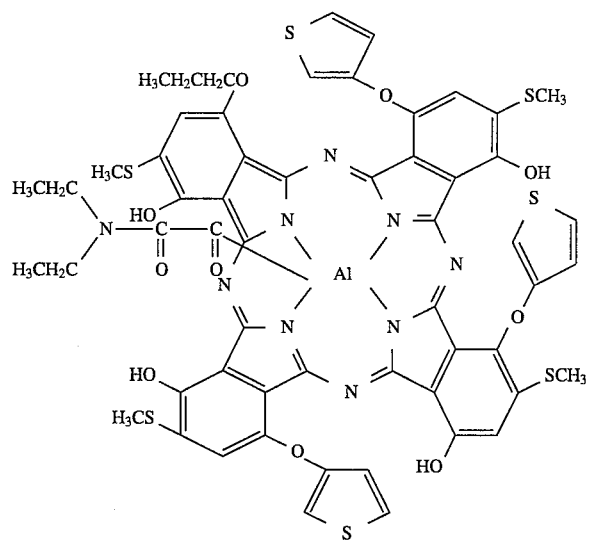 |
| (28) | 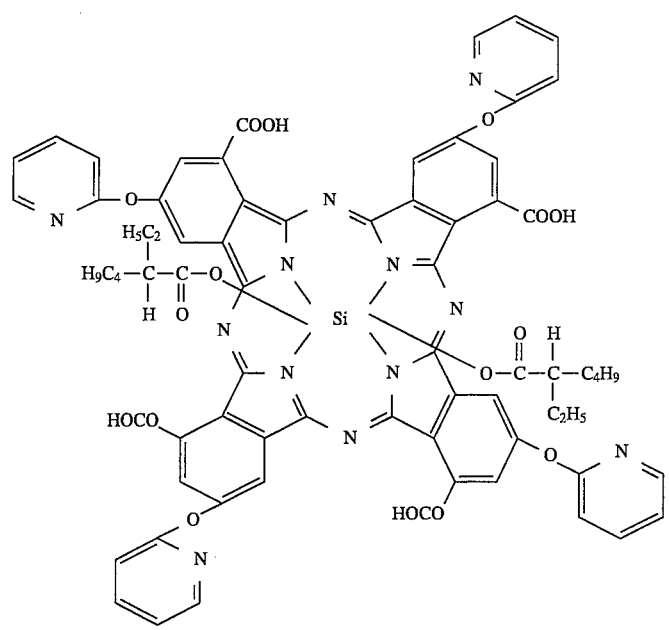 |

-continued

| Compound | Chemical Structure |
|---|---|
| (29) | *(structure image)* |
| (30) | *(structure image)* |
| (31) | *(structure image)* |

-continued

| Compound | Chemical Structure |
|---|---|
| (32) | 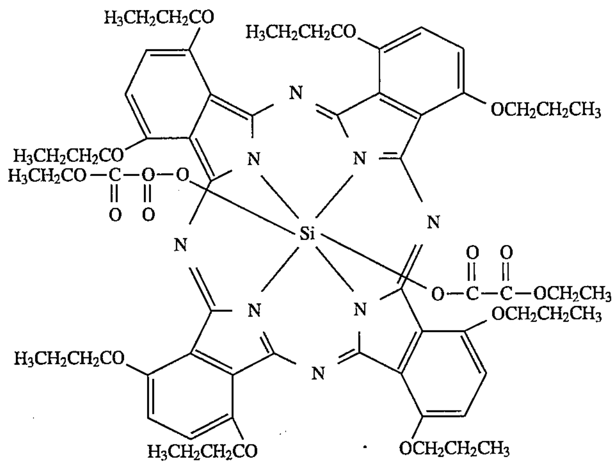 |
| (33) | 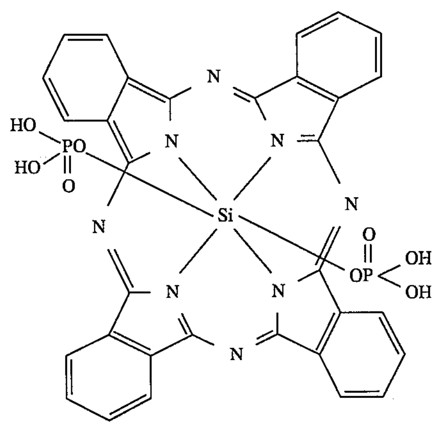 |
| (34) | 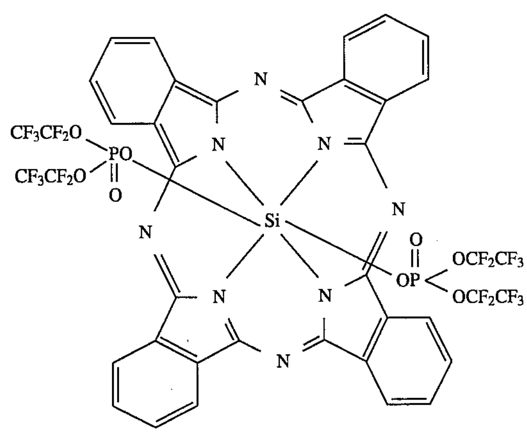 |

-continued

| Compound | Chemical Structure |
|---|---|
| (35) | 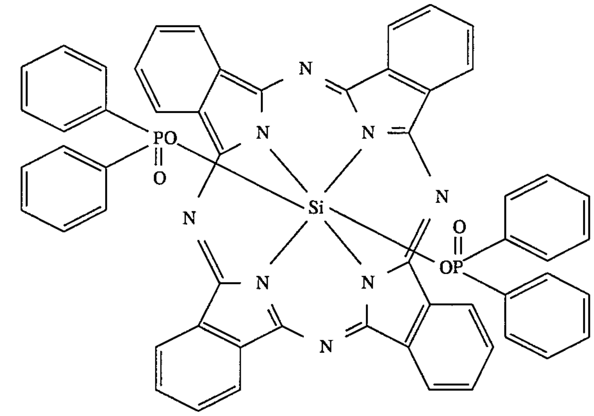 |
| (36) | 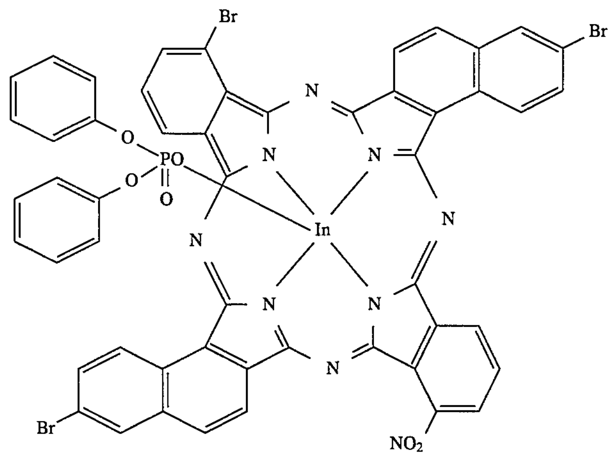 |
| (37) | 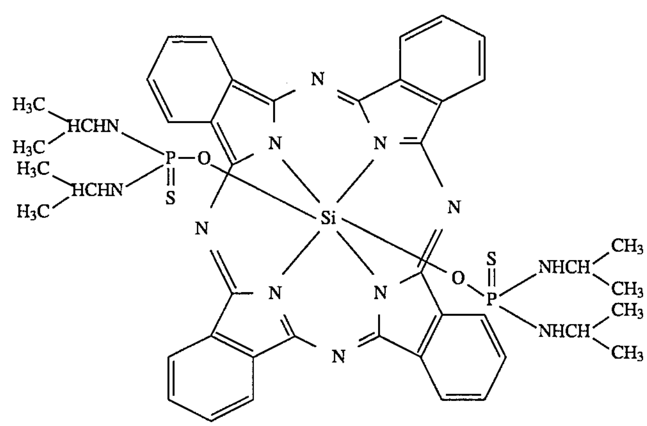 |

| Compound | Chemical Structure |
|---|---|
| (38) | 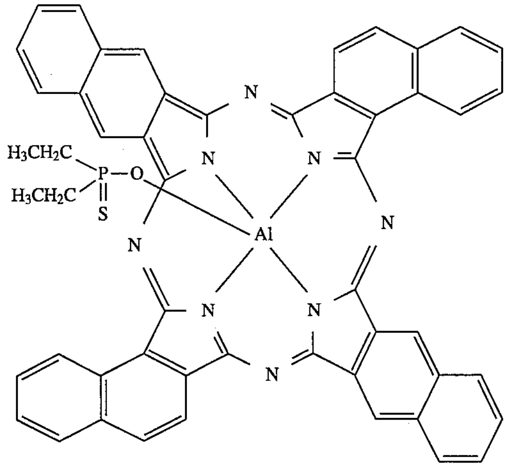 |
| (39) | 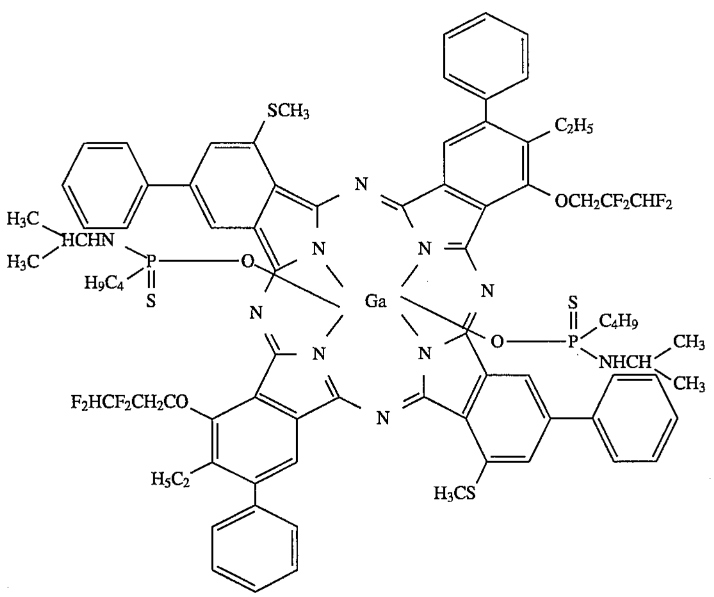 |
| (40) | 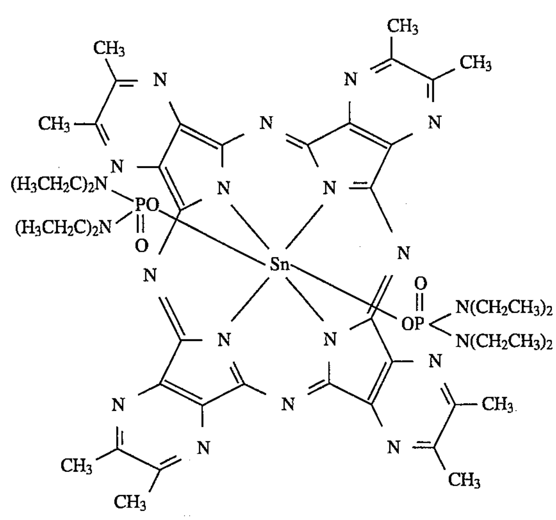 |

| Compound | Chemical Structure |
|---|---|
| (41) | *(complex Si-centered phthalocyanine-type structure with substituents including F₃C-C(CH₃)-H₂CO-, diphenylphosphine oxide groups, and -OCH₂-C(CF₃)₂-CH₃ groups)* |
| (42) | *(complex In-centered naphthalocyanine-type structure with ethyl substituents and a cyclohexyl-P(=O)(=S) group)* |

-continued

| Compound | Chemical Structure |
|---|---|
| (43) | 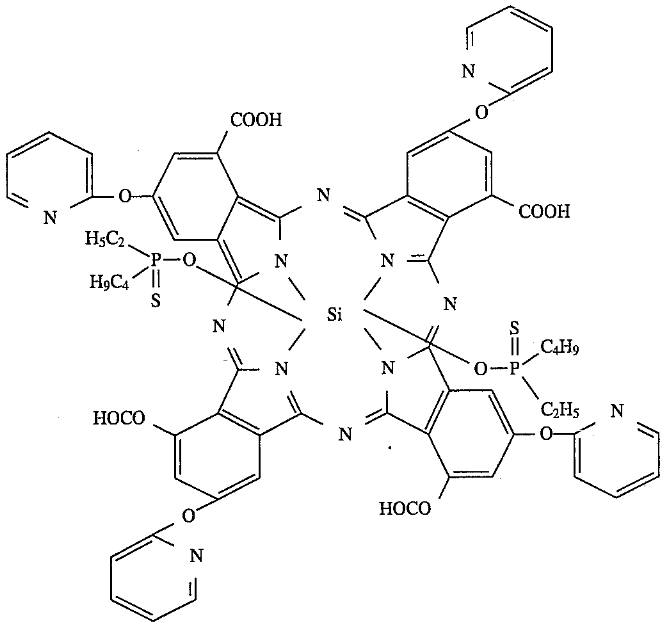 |
| (44) | 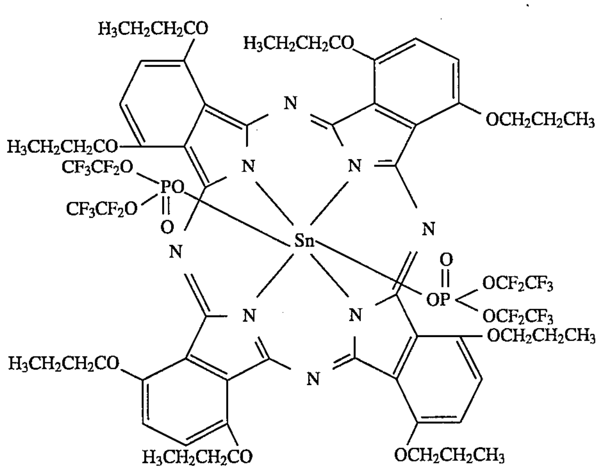 |
| (45) | 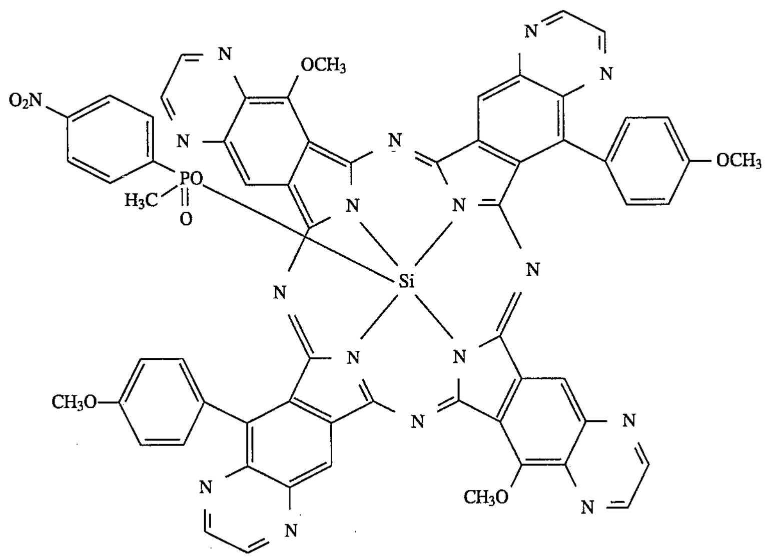 |

-continued
| Compound | Chemical Structure |
|---|---|
| (46) | 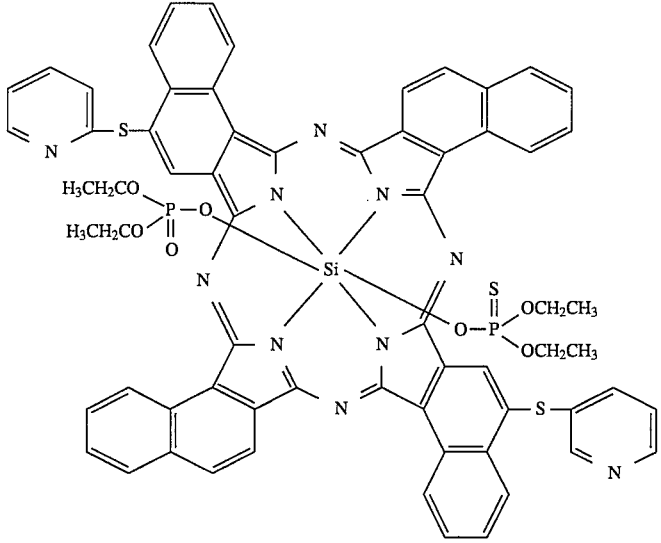 |
| (47) | 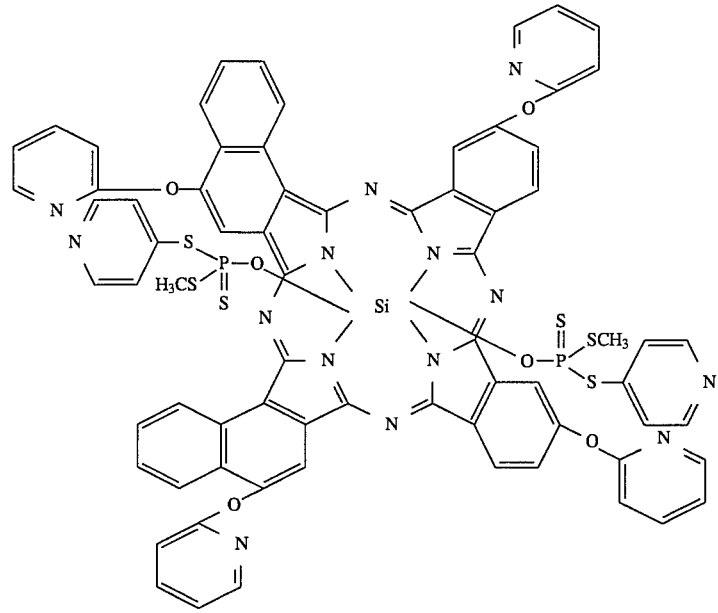 |

| Compound | Chemical Structure |
|---|---|
| (48) | *[Sn porphyrin-like macrocyclic complex with two diphenyl phosphate axial ligands, methyl and cyclohexyl substituents]* |

The above compounds may be used alone or in combination in one layer. Further, the compound of the formula (1) may be used as a mixture with other hole- or electron-transporting compound. The compound of the formula (1), provided by the present invention, is excellent in the hole-transporting capability, and can be very effectively used as a hole-transporting material.

Figure 3:
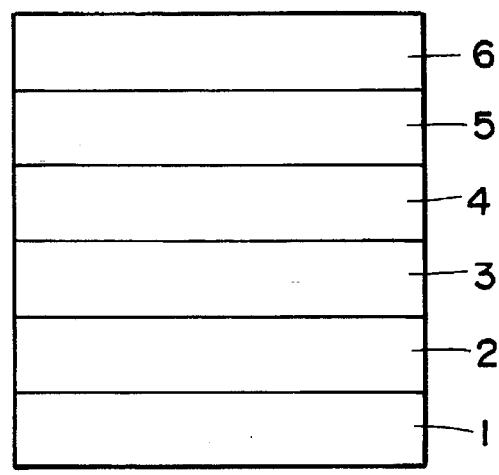
FIG. 3 is a schematic cross section of an organic EL device having a hole-implanting layer, a light-emitting layer and an electron-implanting layer sandwiched between a pair of electrodes.
Figure 2:
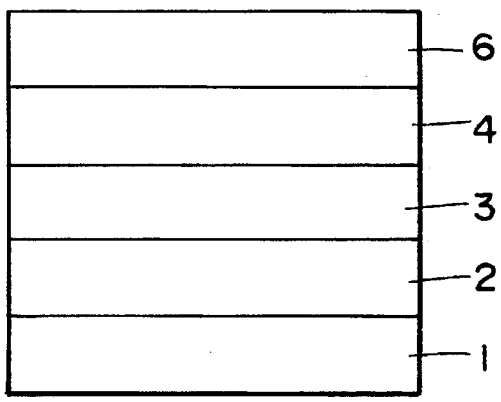
FIG. 2 is a schematic cross section of an organic EL device having a hole-implanting layer and a light-emitting layer sandwiched between a pair of electrodes.

First, the use of the compound of the formula (1) as a hole-transporting material in an organic EL device will be explained below. FIGS. 1 to 3 show schematic cross sections of organic EL device provided by the present invention. In FIGS. 1 to 3, generally, numeral 2 indicates an electrode A (anode) and numeral 6 indicates an electrode B (cathode). Further, numeral 1 indicates a substrate, numeral 3 indicates a hole-implanting layer, numeral 4 indicates a light-emitting layer, and numeral 5 indicates an electron-implanting layer. The compound of the formula (1) may be used in any one of device constitutions as shown in FIGS. 1 to 3.

The compound of the formula (1) has high hole-transporting capability so that it can be used in any one of the hole-implanting layer 3, the light-emitting layer 4 and the electron-implanting layer, as a hole-transporting material.

In the light-emitting layer 4 in FIG. 1, a light-emitting substance, a light-emitting auxiliary material, a hole-transporting material and an electron-transporting material may be used in addition to the compound of the formula (1) as required.

In the structure shown in FIG. 2, the light-emitting layer 4 and the hole-implanting layer 3 are provided as separate ones. In this structure, the efficiency of the implantation of holes from the hole-implanting layer 3 to the light-emitting layer 4 is improved, so that the light emission brightness and the light emission efficiency can be increased. In this constitution, it is desirable for light emission efficiency that the light-emitting substance used in the light-emitting layer be capable of transporting electrons or that the light-emitting layer be made capable of transporting electrons by incorporating an electron-transporting material in to the light-emitting layer.

In the structure shown in FIG. 3, the electron-implanting layer 5 is provided in addition to the hole-implanting layer 3, for improving the efficiency of the recombination of holes and electrons in the light-emitting layer 4. The multi-layered structure of an organic EL device as shown in FIG. 3 can prevent quenching from decreasing the brightness and life of the organic EL device. In the devices shown in FIGS. 2 and 3, a light-emitting substance, a light-emitting auxiliary material, a hole-transporting material for transporting a carrier, and an electron-transporting material may be used in combination. Further, each of the hole-implanting layer, the light-emitting layer and the electron-implanting layer may have a structure of at least two layers.

The electrically conductive material used as an anode of the organic EL device preferably has a work function of greater than 4 eV, and it is selected from carbon, aluminum, vanadium, iron, cobalt, nickel, tungsten, silver, gold, platinum, palladium, alloys of these, metal oxides such as tin oxide and indium oxide called an ITO substrate or an NESA substrate, and organic electrically conductive resins such as polythiophene and polypyrrole.

The electrically conductive material used as a cathode preferably has a work function of smaller than 4 eV. Although not specially limited, it is selected from magnesium, calcium, tin, lead, titanium, yttrium, lithium, ruthenium, manganese and alloys of these. Each of the anode and the cathode may have a structure of at least two layers.

For achieving efficient light emission of the organic EL device, at least one of the electrode A (indicated by 2) and the electrode B (indicated by 6) is transparent preferably in the region of light emission wavelength of the device. Further, the substrate 1 is preferably transparent. The transparent electrode is formed from the above electrically conductive material by a deposition method or a sputtering method, such that it has a predetermined transparency. The electrode through which light is emitted preferably has a transmissivity of at least 10%.

The substrate 1 is not specially limited if it has mechanical strength and thermal strength and is transparent, and it is selected from a glass substrate, and transparent resin substrates such as a polyethylene substrate, a polyethersulfone substrate and a polypropylene substrate.

Each layer of the organic EL device of the present invention can be produced by any one of dry film forming methods such as a vacuum deposition method and a sputtering method and wet film forming methods such as a spin coating method and a dipping method. The thickness of each layer is not specially limited, while each layer is required to have a proper thickness. If the thickness is too large, inefficiently, it is required to apply a high voltage for obtaining a proper optical output. When the film thickness is too small, pin holes are liable to occur so that no sufficient brightness is obtained under a proper electric field. The thickness of each layer is preferably 5 nm to 10 μm, more preferably 10 nm to 0.2 μm.

When each film is formed by a wet method, material(s) for each film is dissolved or dispersed in a solvent such as chloroform, tetrahydrofuran, dioxane, or the like, and a thin film is formed. The above solvent is not specially limited. Further, for improving the formability of each organic layer and preventing the formation of pinholes, etc., a proper resin or additive may be used in combination.

The above resin includes insulating resins such as polystyrene, polycarbonate, polyarylate, polyester, polyamide, urethane, polysulfone, polymethyl methacrylate and polymethyl acrylate; photoconductive resins such as poly-N-vinylcarbazole and polysilane; and electrically conductive resins such as polythiophene and polypyrrole.

In the organic EL device of the present invention, the light-emitting layer, the hole-implanting layer and the electron-implanting layer may contain a known light-emitting substance, a known light-emitting auxiliary material, a known hole-transporting material and an electron-transporting material as required in addition to the compound of the formula (1).

The above light-emitting substance or the light-emitting auxiliary material includes anthracene, naphthalene, phenanthrene, pyrene, tethracene, coronene, chrysene flurorescein, perylene, phthaloperylene, naphthaloperylene, perinone, phthaloperinone, naphthaloperinone, diphenylbutadiene, tetraphenylbutadiene, coumarin, oxadiazole, aldazine, bisbenzoxazoline, bisstyryl, pyrazine, cyclopentadiene, oxine, aminoquinoline, imine, diphenylethylene, vinylanthracene, diaminocarbazole, pyran, thiopyran, polymethine, merocyanine, an imidazole chelated oxinoid compound, quinacridone, rubrene and derivatives of these, although the light-emitting substance or the light-emitting auxiliary material shall not be limited to these.

The hole-transporting material that can be used in combination with the hole-transporting material of the formula (1) is selected from those compounds which are capable of transporting holes, which have an excellent effect of implanting holes into the light-emitting layer or the light-emitting substance, which prevent the movement of excitons generated in the light-emitting layer to the electron-implanting layer or the electron-transporting material and which is excellent thin-film formability. Specific examples of the above-specified hole-transporting materials include a phthalocyanine compound, a naphthalocyanine compound, a porphyrin compound, oxadiazole, triazole, imidazole, imidazolone, imidazolthion, pyrazoline, pyrazolone, tetrahydroimidazole, oxazole, oxadiazole, hydrazone, acylhydrazone, polyaryl alkane, stilbene, butadiene, benzidine type triphenylamine, styrylamine type triphenylamine, diamine type triphenylamine, derivatives of these, and polymer materials such as polyvinyl carbazole, polysilane and an electrically conductive polymer, although the hole-transporting material shall not be limited to the above compounds.

The electron-transporting material is selected from those compounds which is capable of transporting electrons, which have an excellent effect of implanting electrons into the light-emitting layer or the light-emitting substance, which prevent the movement of excitons generated in the light-emitting layer to the hole-implanting layer or the hole-transporting material and which has excellent thin-film formability. Examples of the electron-transporting materials include fluorenone, anthraquinodimethane, diphenoquinone, thiopyran dioxide, oxadiazole, perylenetetracarboxylic acid, fluorenylidenemethane, anthrone, and derivatives of these, while the electron-transporting material shall not be limited to the above compounds.

Further, the hole-transporting material may be sensitivity-increased by incorporating an electron-accepting substance, and the electron-transporting material may be sensitivity-increased by incorporating an electron-donating substance.

The compound of the formula (1) provided by the present invention can be used in any one of the layers constituting the organic EL devices shown in FIGS. 1 to 3. Further, the compound of the formula (1) may be used in one layer in combination with at least one of the above light-emitting substance, the above light-emitting auxiliary material, the above hole-transporting material and the above electron-transporting material.

For improving the organic EL device of the present invention in stability against temperature, humidity and ambient atmosphere, the device may be provided with a protection layer on its surface, or the device as a whole may be protected by enclosing the same with silicone oil.

In the present invention, the organic EL device of the present invention exhibits increased light emission efficiency and an increased light emission brightness due to the use of the compound of the formula (1). Further, the organic EL device of the present invention is highly stable against heat and electric current and gives a practically sufficient light emission brightness at a low actuation voltage, so that the deterioration of the organic EL device, a problem of a conventional evice, can be greatly reduced.

The organic EL device of the present invention has high industrial values since it can be adapted for a flat panel display of an on-wall television set, a flat light-emitting device, a light source for copying machines or printers, a light source for liquid crystal displays or counters, a display signboard and a signal light.

The use of the compound of the formula (1), provided by the present invention, for an electrophotographic photoreceptor will be explained hereinafter. The compound of the formula (1) can be used in any layer of an electrophotographic photoreceptor, while it is preferably used as a hole-transporting material since it has high hole-transporting capability. The compound of the formula (1) works as a hole-transporting substance, can very effectively transport charges generated by optical absorption and gives a photoreceptor excellent in fast response. Further, the compound of the formula (1) is excellent in ozone resistance and light stability and therefore can give a photoreceptor having excellent durability.

The electrophotographic photoreceptor is largely classified into a single-layered photoreceptor produced by forming a photosensitive layer of a dispersion of a charge-generating material and an optional charge-transporting material in a binder resin on an electrically conductive substrate, and a laminated photoreceptor produced by laminating an undercoat layer, a charge-generating layer and a hole-transporting layer on an electrically conductive substrate in the order of the undercoat layer, the charge-generating layer and the hole-transporting layer or by laminating a hole-transporting layer and a charge-generating layer on an electrically conductive substrate or an undercoat layer in the order of the hole-transporting layer and the charge-generating layer. The above undercoat layer may be omitted. Further, the photoreceptor may be provided with an overcoat layer for the protection of its surface from activated gas and for the prevention of filming of a toner.

Figure 4:
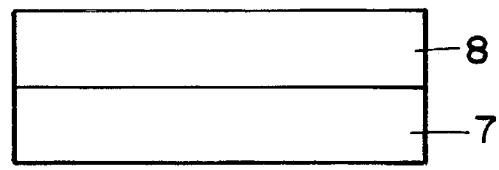
FIG. 4 is a schematic cross section of a single-layered electrophotographic photoreceptor in which a photosensitive layer is formed on an electrically conductive substrate.

FIG. 4 shows a schematic cross section of a single-layered photoreceptor produced by forming a photosensitive layer 8 on an electrically conductive substrate 7.

Figure 5:
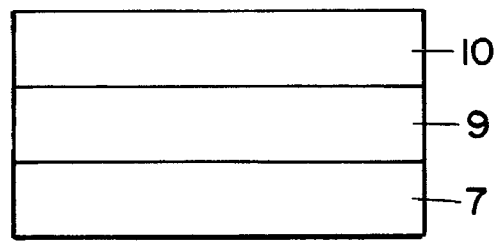
FIG. 5 is a schematic cross section of a laminated electrophotographic photoreceptor in which a charge-generating layer and a hole-transporting layer are consecutively formed on an electrically conductive substrate.

FIG. 5 shows a schematic cross section of a laminated photoreceptor produced by forming a charge-generating layer 9 and a hole-transporting layer 10 on an electrically conductive substrate 7.

The material for the charge-generating layer is selected from organic compounds such as bisazo, quinacridone, indigo, perylene, perinone, polycyclic quinone, squarylium salt, azulenium salt, phthalocyanine and naphthalocyanine, and inorganic substances such as selenium, a selenium-tellurium alloy, cadmium sulfide, zinc oxide and amorphous silicon.

Each layer forming the photoreceptor can be formed by a deposition method or a dispersion application method. The dispersion application may be carried out with a spin coater, an applicator, a spray coater, a dipping coater, a roll coater, a curtain coater or a bead coater. The applied dispersion (coating) may be dried at a temperature between room temperature and 200° C. for 10 minutes to 6 hours optionally under air blowing. When the photoreceptor is a single-layered one, the thickness of the dry photosensitive layer is 5 to 50 μm. When the photoreceptor is a laminated one, the thickness of the charge-generating layer is 0.01 to 5μ, preferably 0.1 to 1 μm, and the thickness of the hole-transporting layer is 5 to 50 μm, preferably 10 to 20 μm.

The resin used for forming the photosensitive layer of the single-layered photoreceptor or forming the charge-generating layer or the hole-transporting layer of the laminated photoreceptor can be selected from a broad range of insulating resins. Further, the above resin can be also selected from organic photoconductive polymers such as poly-N-vinylcarbozole, polyvinyl anthracene and polysilanes. The above resin is preferably selected from insulating resins such as polyvinyl butyral, polyarylate, polycarbonate, polyester, phenoxy, acryl, polyamide, urethane, epoxy, silicone, polystyrene, polyvinyl chloride, vinyl chloride-vinyl acetate copolymer, phenol and melamine resins. Although not specially limited, the amount of the resin used for forming the charge-generating layer or the hole-transporting layer is preferably 100% by weight or less based on the weight of the charge-generating material or the hole-transporting material. The above resins may be used alone or in combination. Further, if necessary, no resin may be used. Further, the charge-generating layer may be formed by a physical film-forming method such as a deposition or sputtering method. In the deposition or sputtering method, the charge-generating layer is preferably formed in an atmosphere under a vacuum of $10^{-5}$ Torr or less. Further, the charge-generating layer may be formed in an inert gas such as nitrogen, argon or helium.

The solvent used for forming each layer of the electrophotographic photoreceptor is preferably selected from those solvents which have no influence on the undercoat layer and other photosensitive layer. Specifically, the above solvent is selected from aromatic hydrocarbons such as benzene and xylene, ketones such as acetone, methyl ethyl ketone and cyclohexanone, alcohols such as methanol and ethanol, esters such as ethyl acetate and methyl cellosolve, halogenated aliphatic hydrocarbons such as carbon tetrachloride, chloroform, dichloromethane, dichloroethane and trichloroethylene, halogenated aromatic hydrocarbons such as chlorobenzene and dichlorobenzene, and ethers such as tetrahydrofuran and dioxane.

The hole-transporting layer is formed by applying the hole-transporting material alone or a solution of the hole-transporting material in the resin. The hole-transporting material for forming the photoreceptor of the present invention may be the compound of the formula (1) alone or a combination of the compound of the formula (1) with other hole-transporting material. The compound of the formula (1) is excellently compatible with other resin and gives almost no precipitate so that it is advantageous for improving the photoreceptor in the sensitivity and durability.

For improving the electrophotographic properties and image proper ties, an undercoat layer may be provided between the substrate and the organic layer. The undercoat layer is formed of a resin selected from polyamides, casein, polyvinyl alcohol, gelatin and polyvinyl butyral or a metal oxide such as aluminum oxide.

The compound of the formula (1) is suitable as a hole-transporting material for electrophotographic photoreceptors of copying machines and printers.

EXAMPLES

The present invention will be explained more in detail hereinafter with reference to Examples, in which "part" stands for "part by weight".

Synthesis of Compound (10)

10 Parts of 4-(1,1,2,2-tetrafluoropropyl)oxy-1,3-diiminoisoindoline and 15 parts of silicon tetrachloride were added to 100 parts of o-dichlorobenzene and 30 parts of tri-n-butylamine, and the mixture was stirred under heat at 160° to 170° C. for 8 hours, then cooled and diluted with 500 parts of methanol. The resultant precipitate was recovered by filtration, washed with a methanol/water (4/1) mixed solution and dried to give 10 parts of a green powder. The green powder was analyzed for a molecular weight to show that the green powder was dihydroxysilicon phthalocyanine coming under the formula (16).

Then, 5 parts of the dihydroxysilicon phthalocyanine was dissolved in 50 parts of 1,1,2,2-tetrafluoropropanol with stirring, and then heated at 110° C. for 10 hours with stirring. The resultant precipitate was recovered by filtration, washed with water and dried to give 4 parts of a green powder. This green powder was analyzed for a molecular weight to show that it was a phthalocyanine compound (10).

The results of elemental analysis of the above product are as follows.

Results of elemental analysis: As $C_{50}H_{30}F_{24}N_8O_6Si$: Calculated (%); C: 45.38, H: 2.27, N: 8.47, Found (%); C: 45.51, H: 2.45, N: 8.12.

Synthesis of Compound (32)

15 Parts of 4,7-(di-n-propyl)oxy-1,3-diiminoisoindoline and 10 parts of silicon tetrachloride were added to 100 parts of o-dichlorobenzene and 30 parts of tri-n-butylamine, and the mixture was stirred under heat at 160° to 170° C. for 8 hours, then cooled and diluted with 500 parts of methanol. The resultant precipitate was recovered by filtration, washed with a methanol/water (4/1) mixed solution and dried to give 9 parts of a green powder. The green powder was analyzed for a molecular weight to show that the green powder was dihydroxysilicon phthalocyanine coming under the formula (16).

Then, 5 parts of the dihydroxysilicon phthalocyanine was dissolved in 50 parts of ethyloxalyl chloride and 100 parts of pyridine with stirring, and then heated at 110° C. for 10 hours with stirring. The resultant precipitate was recovered by filtration, washed with water and dried to give 4 parts of a green powder. This green powder was analyzed for a molecular weight to show that it was a phthalocyanine compound (32).

The results of elemental analysis of the above product are as follows.

Results of elemental analysis: As $C_{64}H_{74}N_8O_{16}Si$: Calculated (%); C: 62.03, H: 5.98, N: 9.05, Found (%); C: 62.32, H: 6.05, N: 9.12.

Synthesis of Compound (41)

10 Parts of 4-(2,2-bis(trifluoromethyl)propyl)oxy-1,3-di-iminoisoindoline and 15 parts of silicon tetrachloride were added to 100 parts of o-dichlorobenzene and 30 parts of tri-n-butylamine, and the mixture was stirred under heat at 160° to 170° C. for 8 hours, then cooled and diluted with 500 parts of methanol. The resultant precipitate was recovered by filtration, washed with a methanol/water (4/1) mixed solution and dried to give 10 parts of a green powder. The green powder was analyzed for a molecular weight to show that the green powder was dihydroxysilicon phthalocyanine coming under the formula (16).

Then, 5 parts of the above-obtained dihydroxysilicon phthalocyanine was dissolved in 100 parts of pyridine and 25 parts of n-tributylamine with stirring, and then 10 parts of chlorodiphenyl phosphine was added with cooling. The mixture was heated at 100° C. for 2 hours with stirring. Then, the resultant precipitate was recovered by filtration, washed with water and dried to give 4 parts of a phthalocyanine compound. This compound was analyzed for a molecular weight to show that it was a phthalocyanine compound (41).

The results of elemental analysis of the above product are as follows.

Results of elemental analysis: As $C_{76}H_{52}F_{24}N_8O_8P_2Si$: Calculated (%); C: 52.11, H: 2.97, N: 6.40, Found (%); C: 52.42, H: 2.51, N: 6.27.

EXAMPLE 1

Compound (4), a tris(8-hydroxyquinoline) aluminum complex and a polycarbonate resin (PC-A) in a weight ratio of 3:2:5 were dissolved in tetrahydrofuran, and the resultant solution was applied to a washed glass plate with an ITO electrode by a spin coating method to form a light-emitting layer having a thickness of 100 nm. An electrode having a thickness of 150 nm was formed on the light-emitting layer from an alloy of magnesium and silver in a magnesium:silver ratio of 10:1, to give an organic EL device as shown in FIG. 1. This organic EL device showed a light emission of 180 cd/m² at a direct-current voltage of 10 V.

EXAMPLE 2

Compound (1) was dissolved in tetrahydrofuran, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device as shown in FIG. 2. The above light-emitting layer was formed by deposition in a vacuum of $10^{-6}$ Torr with a substrate temperature set at room temperature. This organic EL device showed a light emission of about 250 cd/m² at a direct-current voltage of 10 V.

EXAMPLE 3

Compound (10) was dissolved in tetrahydrofuran, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device as shown in FIG. 2. The above light-emitting layer was formed by deposition in a vacuum of $10^{-6}$ Torr with a substrate temperature set at room temperature. This organic EL device showed a light emission of about 410 cd/m² at a direct-current voltage of 10 V.

EXAMPLE 4

Compound (3) was vacuum-deposited on a washed glass plate with an ITO electrode to form a hole-implanting layer having a thickness of 20 nm. Further, N,N'-diphenyl-N,N'-(3-methylphenyl)-1,1'-biphenyl-4,4'-diamine was vacuum-deposited to form a hole-transporting layer having a thickness of 30 nm. Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device. The above hole-implanting layer and the above light-emitting layer were formed by deposition in a vacuum of $10^{-6}$ Torr with a substrate temperature set at room temperature. This organic EL device showed a light emission of about 310 cd/m² at a direct-current voltage of 10 V.

EXAMPLE 5

N,N'-diphenyl-N,N'-(3-methylphenyl)-1,1'-biphenyl-4,4'-diamine was vacuum-deposited on a washed glass plate with an ITO electrode to form a hole-implanting layer having a thickness of 50 nm. Then, a tris(8-hydroxyquinoline) aluminum complex and Compound (2) were vacuum-deposited in a complex:Compound (2) amount ratio of 3:1 to form a light-emitting layer having a thickness of 50 nm. An electrode having a thickness of 150 nm was formed on the light-emitting layer from an alloy of magnesium and silver in a magnesium:silver mixing ratio of 10:1, to give an organic EL device as shown in FIG. 2. The above hole-implanting and the above light-emitting layer were formed by deposition in a vacuum of $10^{-6}$ Torr with a substrate temperature set at room temperature. This organic EL device showed a light emission of about 270 cd/m² at a direct-current voltage of 10 V.

EXAMPLE 6

Compound (13) was dissolved in chloroform, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 50 nm. Further, 2-(4-tert-butylphenyl)-5-(biphenyl)-1,3,4-oxadiazole was vacuum-deposited to form an electron-implanting layer having a thickness of 20 nm. An electrode having a thickness of 150 nm was formed thereon from an alloy of magnesium and silver in a magnesium:silver mixing ratio of 10:1, to give an organic EL device as shown in FIG. 3. This organic EL device showed a light emission of about 290 $cd/m^2$ at a direct-current voltage of 10 V.

EXAMPLE 7

Compound (20), a tris(8-hydroxyquinoline) aluminum complex and a polycarbonate resin (PC-A) in a Compound (20):complex:polycarbonate resin amount ratio of 3:2:5 were dissolved in a tetrahydrofuran, and the resultant solution was applied to a washed glass plate with an ITO electrode by a spin coating method to form a light-emitting layer having a thickness of 100 nm. An electrode having a thickness of 150 nm was formed thereon from an alloy of magnesium and silver in a magnesium:silver mixing ratio of 10:1, to give an organic EL device as shown in FIG. 1. This organic EL device showed a light emission of about 180 $cd/m^2$ at a direct-current voltage of 10 V.

EXAMPLE 8

Compound (17) was dissolved in tetrahydrofuran, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device as shown in FIG. 2. The above light-emitting layer was formed by deposition in a vacuum of $10^{-6}$ Torr with a substrate temperature set at room temperature. This organic EL device showed a light emission of about 250 $cd/m^2$ at a direct-current voltage of 10 V.

EXAMPLE 9

Compound (26) was dissolved in tetrahydrofuran, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device as shown in FIG. 2. The above light-emitting layer was formed by deposition in a vacuum of $10^{-6}$ Torr with a substrate temperature set at room temperature. This organic EL device showed a light emission of about 410 $cd/m^2$ at a direct-current voltage of 10 V.

EXAMPLE 10

Compound (19) was vacuum-deposited on a washed glass plate with an ITO electrode to form a hole-implanting layer having a thickness of 20 nm. Further, N,N'-diphenyl-N,N'-(3-methylphenyl)-1,1'-biphenyl-4,4'-diamine was vacuum-deposited to form a hole-transporting layer having a thickness of 30 nm. Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device. The above hole-implanting layer and the above light-emitting layer were formed by deposition in a vacuum of $10^{-5}$ Torr with a substrate temperature set at room temperature. This organic EL device showed a light emission of about 310 $cd/m^2$ at a direct-current voltage of 10 V.

EXAMPLE 11

N,N'-diphenyl-N,N'-(3-methylphenyl)-1,1'-biphenyl-4,4'-diamine was vacuum-deposited on a washed glass plate with an ITO electrode to form a hole-implanting layer having a thickness of 50 nm. Then, a tris(8-hydroxyquinoline) aluminum complex and Compound (18) were vacuum-deposited in a complex:Compound (18) amount ratio of 3:1 to form a light-emitting layer having a thickness of 50 nm. An electrode having a thickness of 150 nm was formed on the light-emitting layer from an alloy of magnesium and silver in a magnesium:silver mixing ratio of 10:1, to give an organic EL device as shown in FIG. 2. The above hole-implanting layer and the above light-emitting layer were formed by deposition in a vacuum of $10^{-6}$ Torr with a substrate temperature set at room temperature. This organic EL device showed a light emission of about 270 $cd/m^2$ at a direct-current voltage of 10 V.

EXAMPLE 12

Compound (29) was dissolved in chloroform, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 50 nm. Further, 2-(4-tert-butylphenyl)-5-(biphenyl)-1,3,4-oxadiazole was vacuum-deposited to form an electron-implanting layer having a thickness of 20 nm. An electrode having a thickness of 150 nm was formed thereon from an alloy of magnesium and silver in a magnesium:silver mixing ratio of 10:1, to give an organic EL device as shown in FIG. 3. This organic EL device showed a light emission of about 290 $cd/m^2$ at a direct-current voltage of 10 V.

EXAMPLE 13

Compound (36), a tris(8-hydroxyquinoline) aluminum complex and a polycarbonate resin (PC-A) in a Compound (36):complex:polycarbonate resin amount ratio of 3:2:5 were dissolved in a tetrahydrofuran, and the resultant solution was applied to a washed glass plate with an ITO electrode by a spin coating method to form a light-emitting layer having a thickness of 100 nm. An electrode having a thickness of 150 nm was formed thereon from an alloy of magnesium and silver in a magnesium:silver mixing ratio of 10:1, to give an organic EL device as shown in FIG. 1. This organic EL device showed a light emission of about 180 $cd/m^2$ at a direct-current voltage of 10 V.

EXAMPLE 14

Compound (33) was dissolved in tetrahydrofuran, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device as shown in FIG. 2. The above light-emitting layer was formed by deposition in a vacuum of $10^{-6}$ Torr with a substrate temperature set at room temperature. This organic EL device showed a light emission of about 250 $cd/m^2$ at a direct-current voltage of 10 V.

EXAMPLE 15

Compound (42) was dissolved in tetrahydrofuran, and the resultant solution was applied to a washed glass plate with an ITO electrode by a spin coating method to form a hole-implanting layer having a thickness of 50 nm. Then, tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device as shown in FIG. 2. The above light-emitting layer was formed by deposition in a vacuum of $10^{-6}$ Torr with a substrate temperature set at room temperature. This organic EL device showed a light emission of about 410 $cd/m^2$ at a direct-current voltage of 10 V.

EXAMPLE 16

Compound (35) was vacuum-deposited on a washed glass plate with an ITO electrode to form a hole-implanting layer having a thickness of 20 nm. Further, N,N'-diphenyl-N,N'-(3-methylphenyl)-1,1'-biphenyl-4,4'-diamine was vacuum-deposited to form a hole-transporting layer having a thickness of 30 nm, Then, a tris(8-hydroxyquinoline) aluminum complex was vacuum-deposited to form a light-emitting layer having a thickness of 30 nm. An electrode having a thickness of 100 nm was formed on the light-emitting layer from an alloy of magnesium and silver in a magnesium:silver mixing ratio of 10:1, to give an organic EL device. The above hole-implanting layer and the above light-emitting layer were formed by deposition in a vacuum of $10^{-6}$ Torr with a substrate temperature set at room temperature. This organic EL device showed a light emission of about 310 $cd/m^2$ at a direct-current voltage of 10 V.

EXAMPLE 17

N,N'-diphenyl-N,N'-(3-methylphenyl)-1,1'-biphenyl-4,4'-diamine was vacuum-deposited on a washed glass plate with an ITO electrode to form a hole-implanting layer having a thickness of 50 nm. Then, a tris(8-hydroxyquinoline) aluminum complex and Compound (34) were vacuum-deposited in a complex:Compound (34) amount ratio of 3:1 to form a light-emitting layer having a thickness of 50 nm. An electrode having a thickness of 150 nm was formed on the light-emitting layer from an alloy of magnesium and silver in a magnesium:silver mixing ratio of 10:1, to give an organic EL device as shown in FIG. 2. The above hole-implanting layer and the above light-emitting layer were formed by deposition in a vacuum of $10^{-6}$ Torr with a substrate temperature set at room temperature. This organic EL device showed a light emission of about 270 $cd/m^2$ at a direct-current voltage of 10 V.

EXAMPLE 18

Compound (45) was dissolved in chloroform, and the resultant solution was applied to a washed glass plate with an ITO electrode by a spin coating method to form a hole-implanting layer having a thickness of 50 nm. Then, a tris(8-hydroxyquinoline) aluminum complex was vacuum-deposited to form a light-emitting layer having a thickness of 50 nm. Further, 2-(4-tert-butylphenyl)-5-(biphenyl)-1,3,4-oxadiazole was vacuum-deposited to form an electron-implanting layer having a thickness of 20 nm. An electrode having a thickness of 150 nm was formed thereon from an alloy of magnesium and silver in a magnesium:silver mixing ratio of 10:1, to give an organic EL device as shown in FIG. 3. This organic EL device showed a light emission of about 290 $cd/m^2$ at a direct-current voltage of 10 V.

When all the organic EL devices obtained in the above Examples were allowed to emit light continuously at 1 $mA/cm^2$, all the organic EL devices emitted light stability for more than 1,000 hours.

The organic EL device of the present invention shows improved light emission efficiency and improved light emission brightness and accomplishes a longer life of the device, and shall not have any limitation to be imposed on the light-emitting substance, the light-emitting auxiliary material, the hole-transporting material, the electron-transporting material, the sensitizer, the resin and the electrode materials used together with the compound of the formula 1, nor shall it have any limitation to be imposed on the method of producing the device.

EXAMPLE 19

4 Grams of ε-form copper phthalocyanine, 2 g of Compound (4) and 14 g of a polyester resin (Vylon 200, supplied by Toyobo Co. , Ltd. ) were dispersed together with 80 g of tetrahydrofuran with a ball mill for 5 hours. The resultant dispersion was applied to an aluminum substrate and dried to give a single-layered electrophotographic photoreceptor having a thickness of 15 µm, as schematically shown in FIG. 4.

EXAMPLE 20

6 Grams of dibromoanthanthrone, 2 g of Compound (11) and 12 g of a polyester resin (Vylon 200, supplied by Toyobo Co., Ltd.) were dispersed together with 80 g of tetrahydrofuran with a ball mill for 5 hours. The resultant dispersion was applied to an aluminum substrate and dried to give a single-layered electrophotographic photoreceptor having a thickness of 15 µm, as schematically shown in FIG. 4.

EXAMPLE 21

2 Grams of υ-form metal-free phthalocyanine and 2 g of a polyvinyl butyral resin (BH-3, supplied by Sekisui Chemical Co., Ltd.) were dispersed together with 96 g of tetrahydrofuran with a ball mill for 2 hours. The resultant dispersion was applied to an aluminum substrate and dried to form a charge-generating layer having a thickness of 0.3 µm. Then, 10 g of Compound (5) and 10 g of a polycarbonate resin (L-1250, supplied by Teijin Chemical Ltd.) were dissolved in 80 g of dichloromethane. The resultant solution was applied onto the charge-generating layer and dried to form a charge-transporting layer having a thickness of 20 μm, whereby a laminated electrophotographic photoreceptor as schematically shown in FIG. 5 was obtained.

EXAMPLE 22

2 Grams of N,N'-bis(2-carboxymethoxyphenyl)-3,4,9,10-perylenedicarboxyimide and 2 g of a polyvinyl butyral resin (BH-3, supplied by Sekisui Chemical Co., Ltd.) were dispersed together with 96 g of tetrahydrofuran with a ball mill for 2 hours. The resultant dispersion was applied to an aluminum substrate and dried to form a charge-generating layer having a thickness of 0.3 μm. Then, 10 g of Compound (10) and 10 g of a polycarbonate resin (L-1250, supplied by Teijin Chemical Ltd.) were dissolved in 80 g of dichloromethane. The resultant solution was applied onto the charge-generating layer and dried to form a charge-transporting layer having a thickness of 20 μm, whereby a laminated electrophotographic photoreceptor as schematically shown in FIG. 5 was obtained.

EXAMPLE 23

4 Grams of ε-form copper phthalocyanine, 2 g of Compound (20) and 14 g of a polyester resin (Vylon 200, supplied by Toyobo Co., Ltd.) were dispersed together with 80 g of tetrahydrofuran with a ball mill for 5 hours. The dispersion was applied to an aluminum substrate and dried to give a single-layered electrophotographic photoreceptor having a thickness of 15 μm, as schematically shown in FIG. 4.

EXAMPLE 24

6 Grams of dibromoanthanthrone, 2 g of Compound (27) and 12 g of a polyester resin (Vylon 200, supplied by Toyobo Co., Ltd. ) were dispersed together with 80 g of tetrahydrofuran with a ball mill for 5 hours. The resultant dispersion was applied to an aluminum substrate and dried to give a single-layered electrophotographic photoreceptor having a thickness of 15 μm, as schematically shown in FIG. 4.

EXAMPLE 25

2 Grams of υ-form metal-free phthalocyanine and 2 g of a polyvinyl butyral resin (BH-3, supplied by Sekisui Chemical Co., Ltd.) were dispersed together with 96 g of tetrahydrofuran with a ball mill for 2 hours. The resultant dispersion was applied to an aluminum substrate and dried to form a charge-generating layer having a thickness of 0.3 μm. Then, 10 g of Compound (21) and 10 g of a polycarbonate resin (L-1250, supplied by Teijin Chemical Ltd.) were dissolved in 80 g of dichloromethane. The resultant solution was applied onto the charge-generating layer and dried to form a charge-transporting layer having a thickness of 20 μm, whereby a laminated electrophotographic photoreceptor as schematically shown in FIG. 5 was obtained.

EXAMPLE 26

2 Grams of N,N'-bis(2-carboxymethoxyphenyl)-3,4,9,10-perylenedicarboxyimide and 2 g of a polyvinyl butyral resin (BH-3, supplied by Sekisui Chemical Co., Ltd. ) were dispersed together with 96 g of tetrahydrofuran with a ball mill for 2 hours. The resultant dispersion was applied to an aluminum substrate and dried to form a charge-generating layer having a thickness of 0.3 μm. Then, 10 g of Compound (26) and 10 g of a polycarbonate resin (L-1250, supplied by Teijin Chemical Ltd.) were dissolved in 80 g of dichloromethane. The resultant solution was applied onto the charge-generating layer and dried to form a charge-transporting layer having a thickness of 20 μm, whereby a laminated electrophotographic photoreceptor as schematically shown in FIG. 5 was obtained.

EXAMPLE 27

4 Grams of ε-form copper phthalocyanine, 2 g of Compound (36) and 14 g of a polyester resin (Vylon 200, supplied by Toyobo Co., Ltd.) were dispersed together with 80 g of tetrahydrofuran with a ball mill for 5 hours. The dispersion was applied to an aluminum substrate and dried to give a single-layered electrophotographic photoreceptor having a thickness of 15 μm, as schematically shown in FIG. 4.

EXAMPLE 28

6 Grams of dibromoanthanthrone, 2 g of Compound (43) and 12 g of a polyester resin (Vylon 200, supplied by Toyobo Co., Ltd.) were dispersed together with 80 g of tetrahydrofuran with a ball mill for 5 hours. The resultant dispersion was applied to an aluminum substrate and dried to give a single-layered electrophotographic photoreceptor having a thickness of 15 μm, as schematically shown in FIG. 4.

EXAMPLE 29

2 Grams of υ-form metal-free phthalocyanine and 2 g of a polyvinyl butyral resin (BH-3, supplied by Sekisui Chemical Co., Ltd.) were dispersed together with 96 g of tetrahydrofuran with a ball mill for 2 hours. The resultant dispersion was applied to an aluminum substrate and dried to form a charge-generating layer having a thickness of 0.3 μm. Then, 10 g of Compound (37) and 10 g of a polycarbonate resin (L-1250, supplied by Teijin Chemical Ltd.) were dissolved in 80 g of dichloromethane. The resultant solution was applied onto the charge-generating layer and dried to form a charge-transporting layer having a thickness of 20 μm, whereby a laminated electrophotographic photoreceptor as schematically shown in FIG. 5 was obtained.

EXAMPLE 30

2 Grams of N,N'-bis(2-carboxymethoxyphenyl)-3,4,9,10-perylenedicarboxyimide and 2 g of a polyvinyl butyral resin (BH-3, supplied by Sekisui Chemical Co., Ltd.) were dispersed together with 96 g of tetrahydrofuran with a ball mill for 2 hours. The resultant dispersion was applied to an aluminum substrate and dried to form a charge-generating layer having a thickness of 0.3 μm. Then, 10 g of Compound (42) and 10 g of a polycarbonate resin (L-1250, supplied by Teijin Chemical Ltd.) were dissolved in 80 g of dichloromethane. The resultant solution was applied onto the charge-generating layer and dried to form a charge-transporting layer having a thickness of 20 μm, whereby a laminated electrophotographic photoreceptor as schematically shown in FIG. 5 was obtained.

The electrophotographic photoreceptors obtained in the above Examples 19 to 30 were measured for electrophotographic properties as follows. Each photoreceptor was exposed to white light of 5 (lux) with an electrostatic copying paper testing machine (EPA-8100, supplied by Kawaguchi Electric Works) at a static mode 2 at a corona charge of −5.2 (kv) to measure or calculate an initial surface potential ($V_0$), a ratio of a surface potential $V_{(2)}$ after 2 seconds' standing in a dark place to $V_0$ (dark attenuation ratio: $DDR_2=V_2/V_0$), a half exposure dose sensitivity ($E_{1/2}$) based on a time required for a charge amount being decreased to ½ of an initial value after the exposure) and a surface potential after 3 seconds from the exposure ($VR_3$). Table 2 shows the results.

TABLE 2

| Example | $V_0$ (−V) | $DDR_2$ (%) | $E_{1/2}$ (lux.s) | $VR_3$ (−V) |
|---|---|---|---|---|
| 19 | 490 | 95 | 2.5 | 15 |
| 20 | 510 | 97 | 3.1 | 32 |
| 21 | 650 | 98 | 0.9 | 2 |
| 22 | 620 | 98 | 1.1 | 5 |
| 23 | 500 | 96 | 2.7 | 18 |
| 24 | 530 | 98 | 2.9 | 30 |
| 25 | 630 | 95 | 1.2 | 3 |
| 26 | 610 | 98 | 1.0 | 6 |
| 27 | 460 | 92 | 2.4 | 11 |
| 28 | 520 | 98 | 3.2 | 22 |
| 29 | 640 | 96 | 0.8 | 7 |
| 30 | 600 | 96 | 2.1 | 12 |

According to the present invention, there can be obtained compounds having excellent hole-transporting capability. The compounds provided by the present invention enable the production of an organic EL device having higher light emission efficiency, a higher brightness and a longer life than conventional organic EL devices and also enables the production of an electrophotographic photoreceptor which is excellent in initial electrophotographic properties such as sensitivity, hole-transporting capability, an initial surface potential and a dark attenuation ratio and free of fatigue in repetitive use.

What is claimed is:

1. A hole-transporting material of the formula (1),

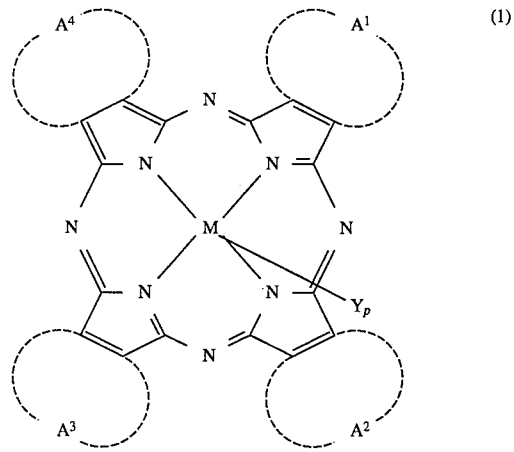

wherein:

each of rings $A^1$ to $A^4$ is a substituted alicyclic group, an unsubstituted alicyclic group, a substituted aromatic group, an unsubstituted aromatic group, a substituted heterocyclic aromatic group, an unsubstituted heterocyclic aromatic group, a substituted heterocyclic ring or an unsubstituted heterocyclic ring, Y is, or each of Ys is independently, a substituent of any one of the formulae (2) to (13), $$-R^1 \quad (2)$$

$$-O-R^2 \quad (3)$$

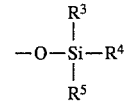

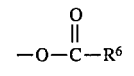

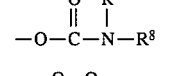

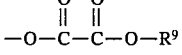

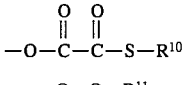

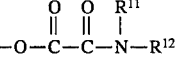

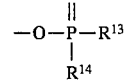

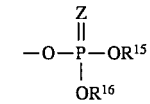

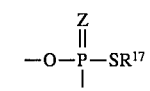

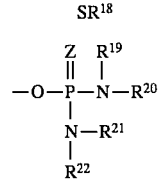

in which each of $R^1$ to $R^{22}$ is independently hydrogen (provided that $R^1$, $R^{13}$ and $R^{14}$ are excluded), a substituted aliphatic group, an unsubstituted aliphatic group, a substituted alicyclic group, an unsubstituted alicyclic group, a substituted aromatic group, an unsubstituted aromatic group, a substituted heterocyclic aromatic group, an unsubstituted heterocyclic aromatic group, a substituted heterocyclic group or an unsubstituted heterocyclic group, and Z is oxygen or sulfur, P is an integer of 1 or 2, and M is a metal atom having a valence of 3 or 4 selected from the group consisting of Al, Ga, Si, Ge and Sn.

2. A hole-transporting material according to claim 1, wherein the alicyclic group is at least one selected from the group consisting of a cyclopentane ring and a cyclohexane ring.

3. A hole-transporting material according to claim 1, wherein the aromatic group is at least one selected from the group consisting of a benzene ring, a naphthalene ring and an anthracene ring.

4. A hole-transporting material according to claim 1, wherein the heterocyclic aromatic group is at least one selected from the group consisting of a pyridine ring, a pyrazine ring, a pyrimidine ring, a triazine ring and a quinoxaline ring.

5. A hole-transporting material according to claim 1, wherein the heterocyclic ring is at least one selected from the group consisting of a pyrrolidine ring, a dioxane ring, a piperidine ring and a morpholine ring.

6. A hole-transporting material according to claim 1, wherein the substituted alicyclic group, the substituted aromatic group, the substituted heterocyclic aromatic group and the substituted heterocyclic ring contains, as a substituent, at least one selected from the group consisting of alkyl, aryl, alkoxy, aryloxy, alkylthio, mono- or disubstituted amino, acylamino, hydroxyl, siloxy, acyl, carbamoyl, a sulfonic group, imido, an alicyclic group, an aromatic group, a heterocyclic aromatic group.

7. An organic electroluminescence device comprising a pair of electrodes and a light-emitting layer of at least one thin film formed of an organic compound, sandwiched between a pair of the electrodes, wherein at least one thin film forming the light-emitting layer contains the hole-transporting material as recited in claim 1.

8. A device according to claim 7, wherein the device comprises the light-emitting layer, a combination of the light-emitting layer and a hole-implanting layer or a combination of the light-emitting, a hole-implanting layer and an electron-implanting layer.

9. A device according to claim 8, wherein at least one of the light-emitting layer, a hole-implanting layer and the electron-implanting layer contains the hole-transporting material as recited in claim 1.

10. An electrophotographic photoreceptor comprising an electrically conductive substrate and a photosensitive layer formed on the substrate, the photosensitive layer containing the hole-transporting material as recited in claim 1.

11. An electrophotographic photoreceptor according to claim 10, wherein the photosensitive layer contains a charge-generating material and the hole-transporting material.

12. An electrophotographic photoreceptor according to claim 10, wherein the photosensitive layer comprises a layer containing a charge-generating layer and a layer containing the hole-transporting material.

* * * * *